US008942782B2

(12) United States Patent
Sakaguchi et al.

(10) Patent No.: US 8,942,782 B2
(45) Date of Patent: Jan. 27, 2015

(54) IMAGE DISPLAY APPARATUS AND RECORDING MEDIUM

(75) Inventors: Yuuichi Sakaguchi, Ashigarakami-gun (JP); Naoyuki Okada, Ashigarakami-gun (JP); Masataka Sugahara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 934 days.

(21) Appl. No.: 12/947,536

(22) Filed: Nov. 16, 2010

(65) Prior Publication Data

US 2011/0116602 A1 May 19, 2011

(30) Foreign Application Priority Data

Nov. 17, 2009 (JP) ................... 2009-262277

(51) Int. Cl.
*A61B 5/05* (2006.01)
*A61B 6/02* (2006.01)
*A61B 6/12* (2006.01)
*A61B 6/00* (2006.01)
(Continued)

(52) U.S. Cl.
CPC . *A61B 6/022* (2013.01); *A61B 6/12* (2013.01); *A61B 6/464* (2013.01); *A61B 6/488* (2013.01); *A61B 6/502* (2013.01); *A61B 6/545* (2013.01); *A61B 6/547* (2013.01); *A61B 10/0233* (2013.01); *A61B 19/203* (2013.01); *A61B 19/50* (2013.01); *A61B 2019/5238* (2013.01); *A61B 2019/5289* (2013.01)
USPC ........... 600/407; 600/426; 600/427; 600/425; 600/461; 378/6; 378/9

(58) Field of Classification Search
USPC ........... 600/407, 461, 426, 427, 425; 378/6, 9
See application file for complete search history.

(56) References Cited

U.S. PATENT DOCUMENTS 6,022,325 A * 2/2000 Siczek et al. ................... 600/568
6,102,866 A * 8/2000 Nields et al. ................... 600/461
(Continued)

FOREIGN PATENT DOCUMENTS

JP 2723257 B2 2/1990
JP 2000-210266 A 8/2000
(Continued)

OTHER PUBLICATIONS

EP Communication, dated Apr. 1, 2011, issued in corresponding EP Application No. 10191300.2, 6 pages.

*Primary Examiner* — Joel Lamprecht
(74) *Attorney, Agent, or Firm* — Sughrue Mion, PLLC

(57) ABSTRACT

An image display apparatus includes a first radiographic image acquirer for acquiring a first radiographic image captured in the scout image capturing process, a second radiographic image acquirer for acquiring a plurality of second radiographic images captured in the stereographic image capturing process, a first display controller for displaying the first radiographic image on a display unit, and a second display controller for displaying the second radiographic images on the display unit and, in case that the biopsy region is selected in the displayed first radiographic image, displaying, in the second radiographic images, respective guide lines passing through positions in the second radiographic images which correspond to the position of the biopsy region selected in the first radiographic image and extending parallel to or substantially parallel to a prescribed direction.

10 Claims, 9 Drawing Sheets

(51) Int. Cl.
*A61B 10/02* (2006.01)
*A61B 19/00* (2006.01)

(56) References Cited

U.S. PATENT DOCUMENTS

| | | | |
|---|---|---|---|
| 6,856,826 B2 * | 2/2005 | Seeley et al. | 600/426 |
| 7,315,638 B2 | 1/2008 | Hara | |
| 7,496,398 B2 * | 2/2009 | Nields et al. | 600/427 |
| 7,828,732 B2 * | 11/2010 | Wang et al. | 600/437 |
| 8,165,660 B2 * | 4/2012 | Pfister et al. | 600/427 |
| 8,200,314 B2 * | 6/2012 | Bladen et al. | 600/427 |
| 2006/0025681 A1 | 2/2006 | Abovitz et al. | |
| 2009/0257551 A1 | 10/2009 | Dafni et al. | |

FOREIGN PATENT DOCUMENTS

| | | |
|---|---|---|
| JP | 2001-190552 A | 7/2001 |
| JP | 2002-102221 A | 4/2002 |
| JP | 2004-105256 A | 4/2004 |
| JP | 2006-280844 A | 10/2006 |
| JP | 2009-136665 A | 6/2009 |

* cited by examiner

IMAGE DISPLAY APPARATUS AND RECORDING MEDIUM

CROSS-REFERENCE TO RELATED APPLICATION

This application is based upon and claims the benefit of priority from Japanese Patent Application No. 2009-262277 filed on Nov. 17, 2009, of which the contents are incorporated herein by reference.

BACKGROUND OF THE INVENTION

1. Field of the Invention

The present invention relates to an image display apparatus and a recording medium.

2. Description of the Related Art

There has heretofore been a technology for displaying a scout image together with a plurality of axial images on a monitor screen and also displaying a line corresponding to one of axial images which is selected over the scout image on the monitor screen (see Japanese Laid-Open Patent Publication No. 2000-210266).

It has been a practice to capture images in a medical test known as biopsy. According to a breast biopsy procedure, a needle is inserted into a breast to sample a tissue of a biopsy region including a suspicious lesion area. In order to insert the needle exactly into the biopsy region, it is necessary to capture images of the biopsy region prior to the needle insertion and determine the position of the biopsy region based on the captured images.

Image capturing processes for biopsy include a scout image capturing process for capturing a single image of a breast and a stereographic image capturing process for capturing a plurality of images of the breast. The doctor or radiological technician who is in charge of a biopsy procedure sees a breast image captured in the scout image capturing process and determines a biopsy region from which a tissue is to be sampled in the captured breast image. Then, a plurality of breast images are captured in the stereographic image capturing process, and the biopsy region is selected in each of the breast images captured in the stereographic image capturing process to determine the three-dimensional position of the biopsy region.

The biopsy region selected in each of the breast images captured in the stereographic image capturing process needs to be identical to the biopsy region determined in the breast image captured in the scout image capturing process. If the biopsy region selected in each of the breast images captured in the stereographic image capturing process is not identical to the biopsy region determined in the breast image captured in the scout image capturing process, then it is not possible to accurately determine the three-dimensional position of the biopsy region captured in the scout image capturing process.

Japanese Laid-Open Patent Publication No. 2000-210266 discloses nothing about the selection in images captured in the stereographic image capturing process of the biopsy region determined in an image captured in the scout image capturing process.

SUMMARY OF THE INVENTION

It is an object of the present invention to provide an image display apparatus and a recording medium which make it easy to select, in images captured in a stereographic image capturing process, a biopsy region which is identical to a biopsy region determined in an image captured in a scout image capturing process.

To achieve the above object, there is provided in accordance with the present invention an image display apparatus comprising a first radiographic image acquirer for acquiring a first radiographic image obtained by a radiation detector that detects radiation having passed through an object to be examined, which includes a biopsy region, and that converts the detected radiation into a radiation image in case that the object to be examined is irradiated by a radiation source which is in a prescribed position and is movable in a prescribed direction with respect to the object to be examined, a second radiographic image acquirer for acquiring a plurality of second radiographic images obtained by the radiation detector in case that the object to be examined is irradiated by the radiation source which is in different positions, a first display controller for displaying the first radiographic image acquired by the first radiographic image acquirer on a first display unit, a biopsy region selector for selecting the biopsy region of the object to be examined which is displayed on the first display unit, and a second display controller for displaying the second radiographic images acquired by the second radiographic image acquirer on a second display unit and, in case that the biopsy region is selected in the displayed first radiographic image by the biopsy region selector, displaying, in the second radiographic images, respective guide lines passing through positions in the second radiographic images which correspond to a position of the biopsy region selected in the first radiographic image and extending parallel to or substantially parallel to the prescribed direction.

When the biopsy region is selected in the displayed first radiographic image by the biopsy region selector, the first display controller displays a distinguishable area based on the position of the selected biopsy region on the first display unit.

The image display apparatus further comprises a biopsy region position calculator for, in case that biopsy regions are selected in at least two of the second radiographic images by a user of the image display apparatus, calculating a three-dimensional position of the biopsy region based on the positions of the selected biopsy regions, and a corresponding position calculator for calculating a corresponding position in the first radiographic image which corresponds to the calculated three-dimensional position of the biopsy region, wherein the first display controller displays a distinguishable area based on the calculated corresponding position.

The image display apparatus further comprises a distance calculator for calculating a distance between the corresponding position calculated by the corresponding position calculator and the position of the biopsy region selected in the first radiographic image by the user, wherein if the distance calculated by the distance calculator is equal to or greater than a predetermined threshold value, the first display controller indicates that the biopsy region selected in the first radiographic image and the biopsy regions selected in the second radiographic images are different from each other.

When the biopsy region of the object to be examined is selected in the first radiographic image by the user of the image display apparatus, the first display controller displays, in the first radiographic image, a line passing through the selected biopsy region and extending parallel to or substantially parallel to the prescribed direction.

The first display unit and the second display unit are provided as a single display unit, and the first display controller and the second display controller display the first radiographic image and the second radiographic images, respectively, in different display areas of the single display unit.

To achieve the above object, there is also provided in accordance with the present invention a recording medium storing a program for enabling a computer to function as a first radiographic image acquirer for acquiring a first radiographic image obtained by a radiation detector that detects radiation having passed through an object to be examined, which includes a biopsy region, and that converts the detected radiation into a radiation image in case that the object to be examined is irradiated by a radiation source which is in a prescribed position and is movable in a prescribed direction with respect to the object to be examined, a second radiographic image acquirer for acquiring a plurality of second radiographic images obtained by the radiation detector in case that the object to be examined is irradiated by the radiation source which is in different positions, a first display controller for displaying the first radiographic image acquired by the first radiographic image acquirer on a first display unit, a biopsy region selector for selecting the biopsy region which is displayed on the first display unit, and a second display controller for displaying the second radiographic images acquired by the second radiographic image acquirer on a second display unit and, in case that the biopsy region is selected in the displayed first radiographic image by the biopsy region selector, displaying, in the second radiographic images, respective guide lines passing through positions in the second radiographic images which correspond to a position of the biopsy region selected in the first radiographic image and extending parallel to or substantially parallel to the prescribed direction.

According to the present invention, when the biopsy region is selected in the displayed first radiographic image by the biopsy region selector, the second display controller displays, in the second radiographic images, respective guide lines passing through positions in the second radiographic images which correspond to the position of the biopsy region selected in the first radiographic image and extending parallel to or substantially parallel to the prescribed directions. Therefore, it is easy to select, in the second radiographic images, the same biopsy regions as the biopsy region selected in the first radiographic image, and the three-dimensional position of the biopsy region selected in the first radiographic image can be calculated with high accuracy.

When the biopsy region is selected in the first radiographic image, since a distinguishable area is displayed based on the position of the selected biopsy region, the user can visually recognize the position of the selected biopsy region.

After the three-dimensional position of the biopsy region is determined based on the positions of the biopsy regions selected in the second radiographic image, the corresponding position in the first radiographic image which corresponds to the determined three-dimensional position is determined, and a distinguishable area is displayed based on the corresponding position in the first radiographic image. Accordingly, the user can visually determine whether the position of the biopsy region selected in the first radiographic image and the positions of the biopsy regions selected in the second radiographic image are identical to each other or not.

If the distance between the calculated corresponding position and the position of the biopsy region selected in the first radiographic image is equal to or greater than a threshold value, then the image display apparatus issues a warning. Therefore, the user is able to recognize that the biopsy region selected in the first radiographic image and the biopsy regions selected in the second radiographic image are different from each other, and hence is prompted to take notice.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
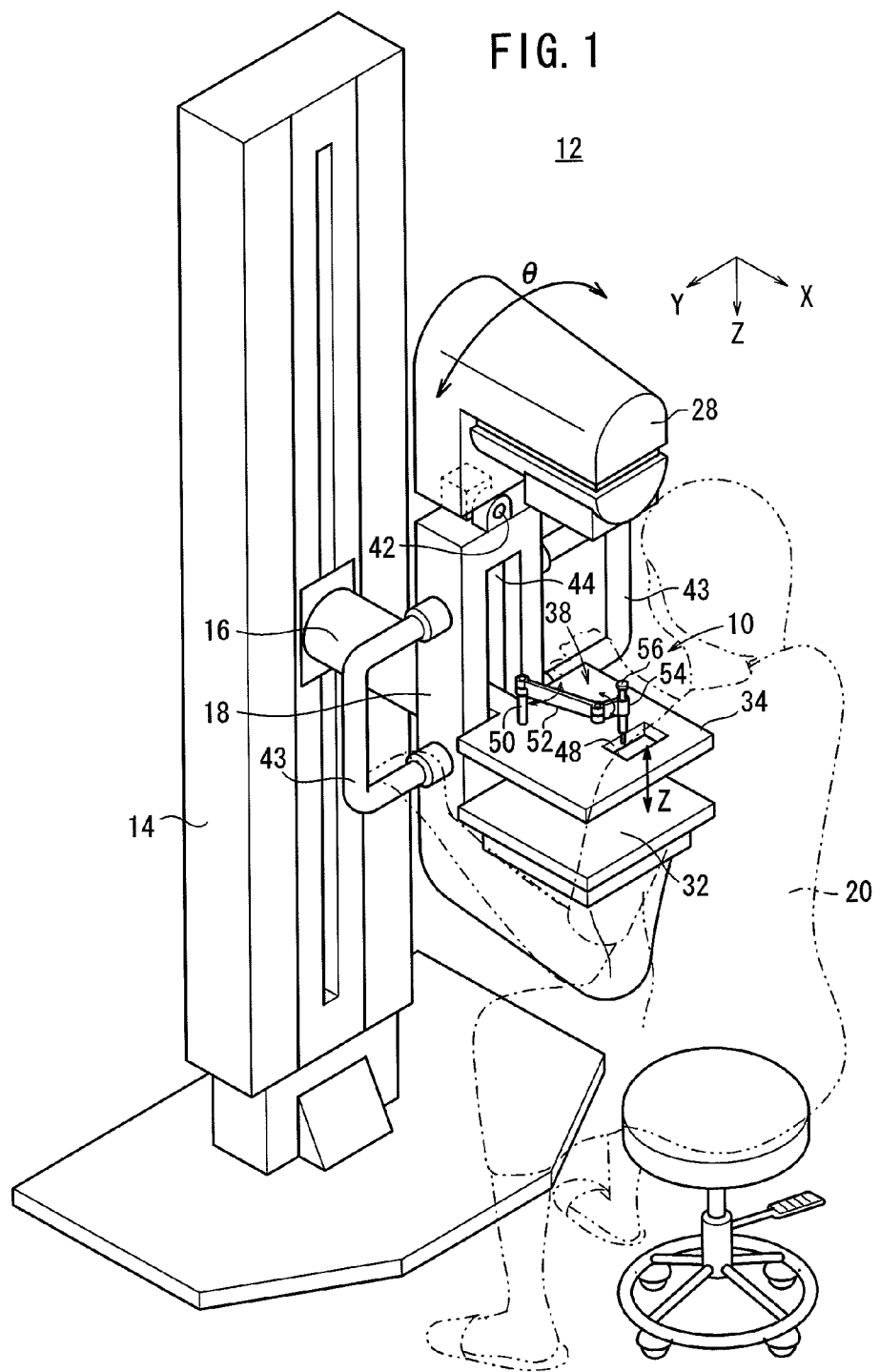
FIG. 1 is a perspective view of a mammographic apparatus incorporating an image display apparatus according to an embodiment of the present invention.

A mammographic apparatus incorporating an image display apparatus according to a preferred embodiment of the present invention will be described in detail below with reference to the accompanying drawings.

The basic structure of a mammographic apparatus (radiographic image capturing apparatus) 12 according to an embodiment of the present invention which incorporates a biopsy apparatus 10 will be described below with reference to FIGS. 1 and 2.

The mammographic apparatus 12 basically includes an upstanding base 14, a vertical arm 18 fixed to the distal end of a swing shaft 16 disposed substantially centrally on the base 14, a radiation source housing unit 28 housing therein a radiation source 26 for applying radiation 24 (see FIG. 2) to a breast 22 as an object to be examined of an examinee (subject) 20 and fixed to an end of the arm 18, an image capturing base 32 mounted on another end of the arm 18 and housing therein a solid-state detector (radiation detector) 30 for detecting the radiation 24 which has passed through the breast 22, a compression plate 34 for compressing and holding the breast 22 against the image capturing base 32, and a biopsy hand assembly 38 for removing a tissue sample from a biopsy region 36 of the breast 22, the biopsy hand assembly 38 being mounted on the compression plate 34.

Figure 2:
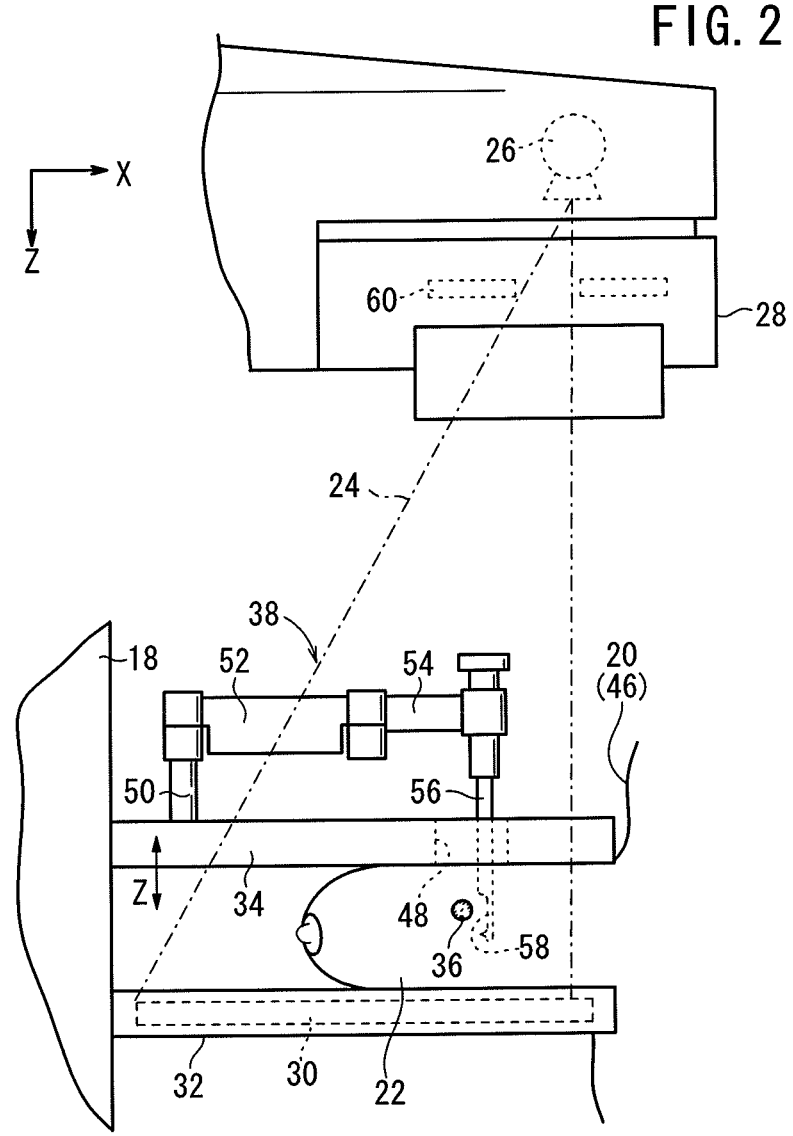
FIG. 2 is an enlarged fragmentary side elevational view of the mammographic apparatus shown in FIG. 1.

In FIGS. 1 and 2, the mammographic apparatus 12 applies the radiation 24 to the breast 22 of the examinee 20 to capture an image thereof and a sample tissue is removed from the biopsy region 36 while the breast 22 of the examinee 20 who is in a sitting position is being compressed and secured by the compression plate 34 and the image capturing base 32.

As shown in FIG. 1, when the arm 18, to which the radiation source housing unit 28 and the image capturing base 32 are secured, is angularly moved about the swing shaft 16, the direction of the radiation source housing unit 28 and the image capturing base 32 with respect to the breast 22 of the examinee 20 is adjusted. The radiation source housing unit 28 is operatively coupled to the arm 18 by a hinge 42 and can be turned about the hinge 42 in the directions indicated by the arrow θ (prescribed direction(s)) independently of the image capturing base 32.

The arm 18 has a groove 44 defined vertically in a side (front side) thereof which faces the examinee 20 in the direction indicated by the arrow X. The groove 44 extends along the direction indicated by the arrow Z. Handles 43 are mounted on the respective sides of the arm 18 which face away from each other along the direction indicated by the arrow Y. The handles 43 are gripped by the examinee 20. As shown in FIGS. 1 and 2, the compression plate 34 has a proximal end inserted in the groove 44 and held in interfitting engagement with a mount, not shown, disposed in the arm 18. The compression plate 34 that is thus coupled to the arm 18 is disposed between the radiation source housing unit 28 and the image capturing base 32. The compression plate 34 is vertically displaceable in unison with the mount along the arm 18 in the directions indicated by the arrow Z when the mount is displaced along the groove 44 in the directions indicated by the arrow Z.

The compression plate 34 has an opening 48 defined therein near a chest wall 46 (see FIG. 2) of the examinee 20, for allowing the biopsy hand assembly 38 to remove a tissue sample from the biopsy region 36 of the breast 22. The biopsy hand assembly 38 serves as part of the biopsy apparatus 10 which is incorporated in the mammographic apparatus 12. The biopsy hand assembly 38 comprises a post 50 fixedly mounted on the compression plate 34, a first arm 52 having an end pivotally supported on the post 50 and angularly movable about the post 50 along the surface of the compression plate 34, and a second arm 54 having an end pivotally supported on the other end of the first arm 52 and angularly movable about the other end of the first arm 52 along the surface of the compression plate 34. A biopsy needle 56 is mounted on the other end of the second arm 54 for movement in the directions indicated by the arrow Z which are perpendicular to the compression plate 34.

As shown in FIG. 2, the biopsy needle 56 has a sampler 58 near the lower end thereof for sampling under suction a tissue (e.g., a calcified tissue) from the biopsy region 36, which is a lesion area (e.g., a calcified area) of the breast 22. The sampler 58 of the biopsy needle 56 can be moved to a position in the vicinity of the biopsy region 36 when the first arm 52 and the second arm 54 of the biopsy hand assembly 38 are moved in an X-Y plane parallel to the surface of the compression plate 34 and the biopsy needle 56 is moved in the directions indicated by the arrow Z.

The radiation source housing unit 28 also houses therein, in addition to the radiation source 26, a collimator 60 for delimiting an irradiated field of the radiation 24 emitted from the radiation source 26.

Figure 3:
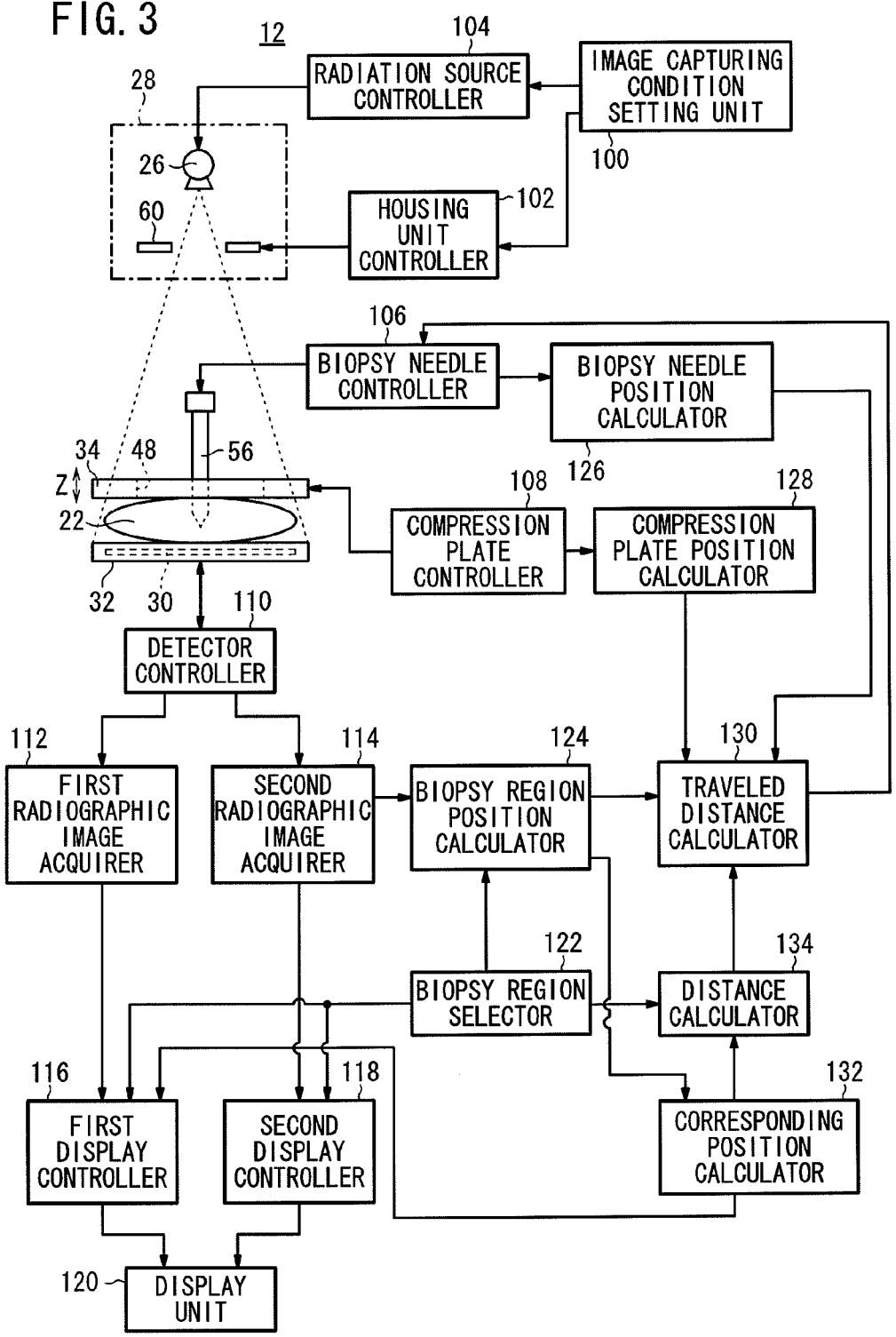
FIG. 3 is an electric block diagram of the mammographic apparatus shown in FIG. 1.

FIG. 3 shows in electric block diagram the mammographic apparatus 12 including the biopsy apparatus 10. As shown in FIG. 3, the mammographic apparatus 12 includes an image capturing condition setting unit 100, a housing unit controller 102, a radiation source controller 104, a biopsy needle controller 106, a compression plate controller 108, a detector controller 110, a first radiographic image acquirer 112, a second radiographic image acquirer 114, a first display controller 116, a second display controller 118, a display unit 120, a biopsy region selector 122, a biopsy region position calculator 124, a biopsy needle position calculator 126, a compression plate position calculator 128, a traveled distance calculator 130, a corresponding position calculator 132, and a distance calculator 134. The electric system of the mammographic apparatus 12 may be functionally implemented by reading a program recorded in a recording medium into an information processor such as a CPU or the like.

The biopsy hand assembly 38, the opening 48, the biopsy needle 56, the biopsy needle controller 106, the biopsy region selector 122, the biopsy needle position calculator 126, and the traveled distance calculator 130 jointly make up the biopsy apparatus 10. The first radiographic image acquirer 112, the second radiographic image acquirer 114, the first display controller 116, the second display controller 118, the display unit 120, the biopsy region selector 122, the biopsy region position calculator 124, the corresponding position calculator 132, and the distance calculator 134 jointly make up an image display apparatus according to the present invention. The biopsy apparatus 10 and the image display apparatus may be of arrangements other than those described above.

The image capturing condition setting unit 100 sets image capturing conditions including doses of the radiation 24, irradiation times, image capturing angles, three-dimensional positions of the radiation source 26, and imaging capturing orders for a scout image capturing process and a stereographic image capturing process. Since an image capturing angle is determined by a three-dimensional position of the radiation source 26, the image capturing condition setting unit 100 may set either one of a three-dimensional position or an image capturing angle of the radiation source 26.

The housing unit controller 102 turns the radiation source housing unit 28 to achieve a set image capturing angle. The doctor or radiological technician (user) in charge may instead manually turn the radiation source housing unit 28. If the doctor or radiological technician manually turns the radiation source housing unit 28, then the image capturing condition setting unit 100 does not set an image capturing angle of the radiation source 26, but the mammographic apparatus 12 has a sensor for detecting the angle of the radiation source housing unit 28 after it has turned, and the biopsy region position calculator 124 acquires the angle of the radiation source housing unit 28 which is detected by the sensor.

The radiation source controller 104 energizes the radiation source 26 according to the image capturing conditions that have been set. The biopsy needle controller 106 controls the biopsy hand assembly 38 (see FIGS. 1 and 2) to move the biopsy needle 56 to a desired position. The compression plate controller 108 moves the compression plate 34 in the directions indicated by the arrow Z. The detector controller 110 controls the solid-state detector 30 to convert the radiation 24 into a radiographic image and acquires the radiation image from the solid-state detector 30. The first radiographic image acquirer 112 acquires a scout radiographic image (first radiographic image) of the breast 22 produced in the scout image capturing process. The second radiographic image acquirer 114 acquires a plurality of radiographic images (second radiographic images) of the breast 22 produced in the stereographic image capturing process.

The first display controller 116 displays the scout radiographic image (first radiographic image) produced in the scout image capturing process on the display unit 120. The second display controller 118 displays two radiographic images (second radiographic images) produced in the stereographic image capturing process on the display unit 120. The first display controller 116 and the second display controller 118 display the radiographic images in respective different display areas of the display unit 120. The second display controller 118 also displays guide lines, to be described later, over the second radiographic images on the display unit 120.

The biopsy region selector 122 comprises a pointing device such as a mouse or the like. The doctor or radiological technician who has seen the displayed contents of the first radiographic image and the second radiographic images on the display unit 120 can select a biopsy region 36, from which a tissue is to be removed, from the radiographic images of the breast 22 displayed on the display unit 120, using the pointing device as the biopsy region selector 122.

The biopsy region position calculator 124 calculates the three-dimensional position of the selected biopsy region 36 based on the positions of the biopsy region 36 selected by the biopsy region selector 122 in the second radiographic images and the image capturing angles of the second radiographic images.

The biopsy needle position calculator 126 calculates the positional information of the tip end of the biopsy needle 56. When a tissue is to be sampled from the biopsy region 36, the biopsy needle position calculator 126 calculates the position of the tip end of the biopsy needle 56 before it samples the tissue from the biopsy region 36, i.e., the position of the tip end of the biopsy needle 56 before it pierces the breast 22.

The compression plate position calculator 128 calculates the position of the compression plate 34 which has been moved with respect to the image capturing base 32 by the compression plate controller 108. Since the compression plate 34 presses the breast 22 with respect to the image capturing base 32 and holds the breast 22 in the pressed state, the position of the compression plate 34 represents the thickness of the breast 22 as it is pressed.

The traveled distance calculator 130 calculates the distance by which the biopsy needle 56 is to move with respect to the biopsy region 36, based on the three-dimensional position of the biopsy region 36 which has been calculated by the biopsy region position calculator 124, the position of the biopsy needle 56 which has been calculated by the biopsy needle position calculator 126, and the position of the compression plate 34 (the thickness of the breast 22) which has been calculated by the compression plate position calculator 128. Based on the calculated distance by which the biopsy needle 56 is to move with respect to the biopsy region 36, the biopsy needle controller 106 moves the biopsy needle 56 for removing a tissue sample from the selected biopsy region 36.

The corresponding position calculator 132 calculates a corresponding position on the first radiographic image which corresponds to the three-dimensional position of the biopsy region 36 which has been calculated by the biopsy region position calculator 124. The corresponding position refers to a two-dimensional position where the biopsy region 36 is present on the first radiographic image if the biopsy region 36 is in the calculated three-dimensional position. In other words, the corresponding position is the position of the biopsy region 36 which appears on the first radiographic image when the radiation source 26 emits the radiation 24 at the image capturing angle in the scout image capturing process.

The distance calculator 134 calculates the difference between the corresponding position calculated by the corresponding position calculator 132 and the position of the biopsy region 36, selected by the biopsy region selector 122, on the first radiographic image.

Figure 4:
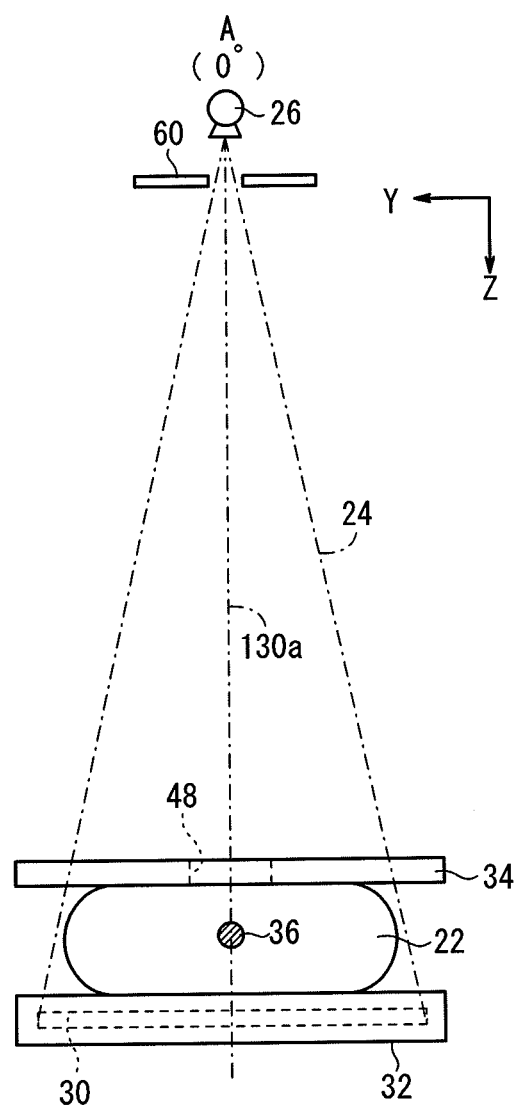
FIG. 4 is a schematic front elevational view showing by way of example a scout image capturing process for capturing a single radiographic image.

The scout image capturing process and the stereographic image capturing process will be described below with reference to FIGS. 4 and 5. FIG. 4 shows by way of example the scout image capturing process which captures a single radiographic image. In the scout image capturing process, the radiation source 26 is located at an image capturing angle of θ=0° with respect to the solid-state detector 30. The image capturing angle of the radiation source 26 with respect to the solid-state detector 30 refers to an angle of the radiation source 26 with respect to a central axis 130a of the solid-state detector 30. The position of the radiation source 26 at the image capturing angle of θ=0° in the scout image capturing process is referred to as "position A". The image capturing angle of the radiation source 26 can be changed when the radiation source housing unit 28 is turned about the hinge 42. Therefore, the image capturing angle of the radiation source 26 changes along the directions indicated by the arrow Y.

Figure 5:
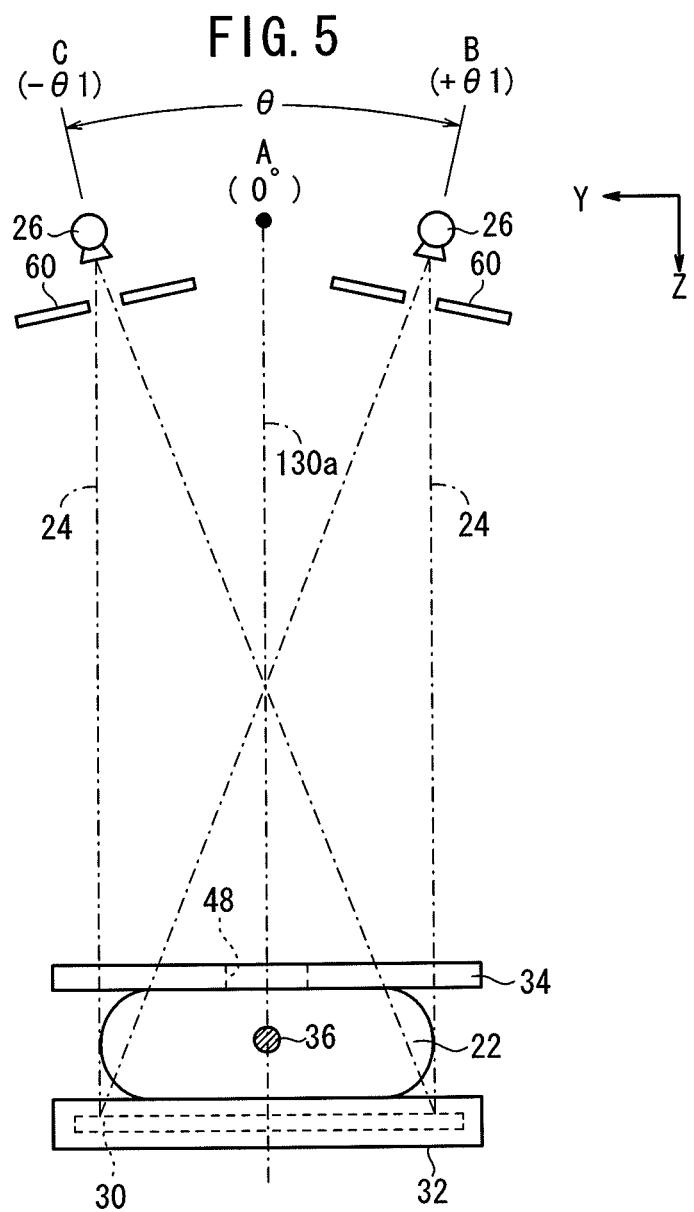
FIG. 5 is a schematic front elevational view showing by way of example a stereographic image capturing process for capturing two radiographic images.

FIG. 5 shows by way of example the stereographic image capturing process for capturing two radiographic images. In the stereographic image capturing process, the radiation source 26 is located at two different image capturing angles of +θ1, −θ1 with respect to the solid-state detector 30. The positions of the radiation source 26 at the respective image capturing angles of +θ1, −θ1 in the stereographic image capturing process are referred to as "position B" and "position C", respectively.

In the scout image capturing process, the mammographic apparatus 12 can produce one radiographic image with the radiation source 26 at one image capturing angle. In the stereographic image capturing process, the mammographic apparatus 12 can produce two radiographic images with the radiation source 26 at respective two image capturing angles.

Figure 6:
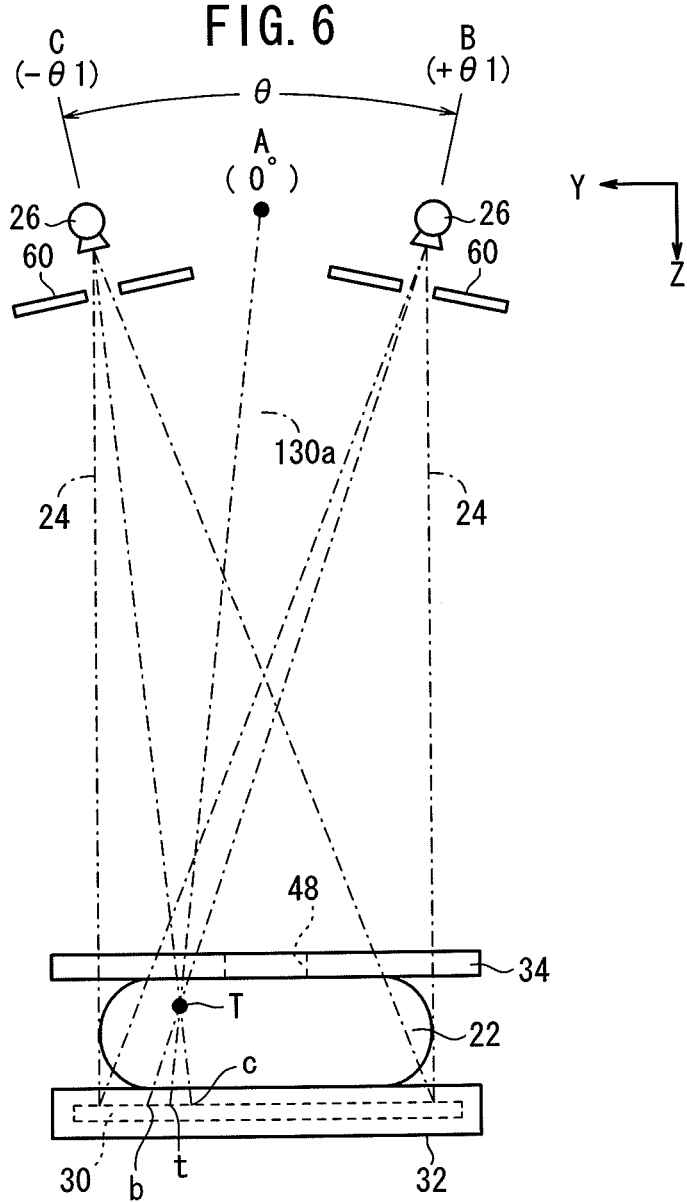
FIG. 6 is a schematic front elevational view illustrative of a process of calculating the three-dimensional position of a biopsy region, which is carried out by a biopsy region position calculator.

The biopsy region position calculator 124 can calculate the three-dimensional position of the biopsy region 36 by way of geometric calculations from the positions of the radiation source 26 in the stereographic image capturing process and the positions of the biopsy region (lesion area) which are designated in the two stereographic images. Specifically, the three-dimensional positions (B, C in FIG. 6) of the radiation source 26 in the stereographic image capturing process are detected by a positional sensor or the like, and actual positions (b, c in FIG. 6) on the solid-state detector 30 which correspond to the positions of the lesion area which are designated in the two stereographic images are determined. The three-dimensional position of the biopsy region 36 is calculated as the intersection (T) of a line Bb and a line Cc. The process of determining actual positions of designated image coordinates on the solid-state detector 30 will not be described below. The intersection (t) (corresponding position) between a straight line passing through the position A of the radiation source 26 in the scout image capturing process and the intersection (T) and the solid-state detector 30 may be displayed in the radiographic image captured in the scout image capturing process. In FIG. 6, the positions of the radiation source 26 and the corresponding positions of the lesion area on the solid-state detector 30 lie on one plane. However, even if these positions do not lie on one plane, e.g., even if the positions of the radiation source 26 are closer to the viewer of FIG. 6 and the corresponding positions of the lesion area on the solid-state detector 30 are remoter from the viewer of FIG. 6, the three-dimensional position of the biopsy region 36 is calculated in the same manner as described above. However, if the lines Bb, Cc do not cross each other in the three-dimensional space, then the midpoint on a shortest line interconnecting the lines Bb, Cc which is representative of the distance between the lines Bb, Cc may be calculated as the three-dimensional position of the biopsy region 36. A certain threshold value may be established for the distance between the lines Bb, Cc, and when the distance between the lines Bb, Cc exceeds the threshold value, a warning may be issued. The three-dimensional position of the biopsy region 36 is given with respect to a certain reference position. For example, three-dimensional position of the biopsy region 36 may be given as coordinates in a coordinate system which has its origin at the central position of the solid-state detector 30.

Figure 7:
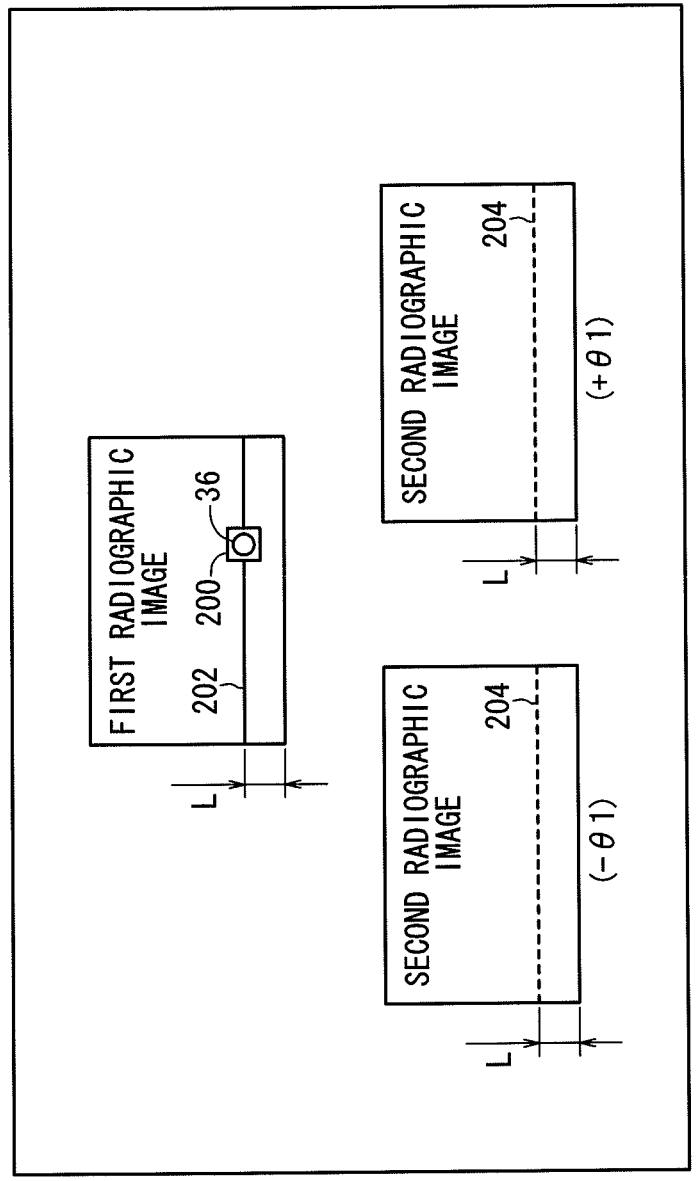
FIG. 7 is a view showing by way of example a screen displayed by a first display controller and a second display controller.

Guide lines displayed over the second radiographic images by the second display controller 118 will be described below. FIG. 7 shows by way of example a screen displayed by the first display controller 116 and the second display controller 118. The first radiographic image is displayed in an upper central area of the screen, and second radiographic images are displayed in lower left and right areas, respectively, of the screen. The second radiographic image displayed in the lower left area is a radiographic image captured when the radiation source 26 is at the image capturing angle of $-\theta1$, and the second radiographic image displayed in the lower right area is a radiographic image captured when the radiation source 26 is at the image capturing angle of $+\theta1$.

The biopsy region 36 displayed in the first radiographic image indicates the biopsy region 36 selected by the biopsy region selector 122. In order to show that the biopsy region 36 has been selected by the doctor or radiological technician, the biopsy region 36 displayed in the first radiographic image is enclosed by a frame 200.

When the biopsy region 36 is selected, the first display controller 116 displays, in the first radiographic image, a line 202 passing through the biopsy region 36 and extending parallel to or substantially parallel to the prescribed directions in which the radiation source 26 can be turned. The second display controller 118 displays, in the second radiographic images, respective guide lines 204 passing through positions in the second radiographic images which correspond to the position of the selected biopsy region 36 in the first radiographic image and extending parallel to or substantially parallel to the prescribed directions in which the radiation source 26 can be turned.

Specifically, if the selected biopsy region 36 is spaced from the lower end of the first radiographic image by a distance L, then the second display controller 118 displays horizontal lines as the guide lines 204 at a position spaced the distance L from the lower ends of the second radiographic images. Since the coordinates of the selected biopsy region 36 in the first radiographic image and the coordinates in the second radiographic images which correspond to the position of the biopsy region 36 are the same as each other, the positions in the second radiographic images which correspond to the position of the selected biopsy region 36 in the first radiographic image are spaced the distance L from the lower ends of the second radiographic images. It is assumed that the first radiographic image and the second radiographic images are identical in size to each other, have horizontal directions oriented substantially along the prescribed directions. The angles $-\theta1$, $+\theta1$ and the distance L are shown for illustrative purposes in FIG. 7.

Figure 8:
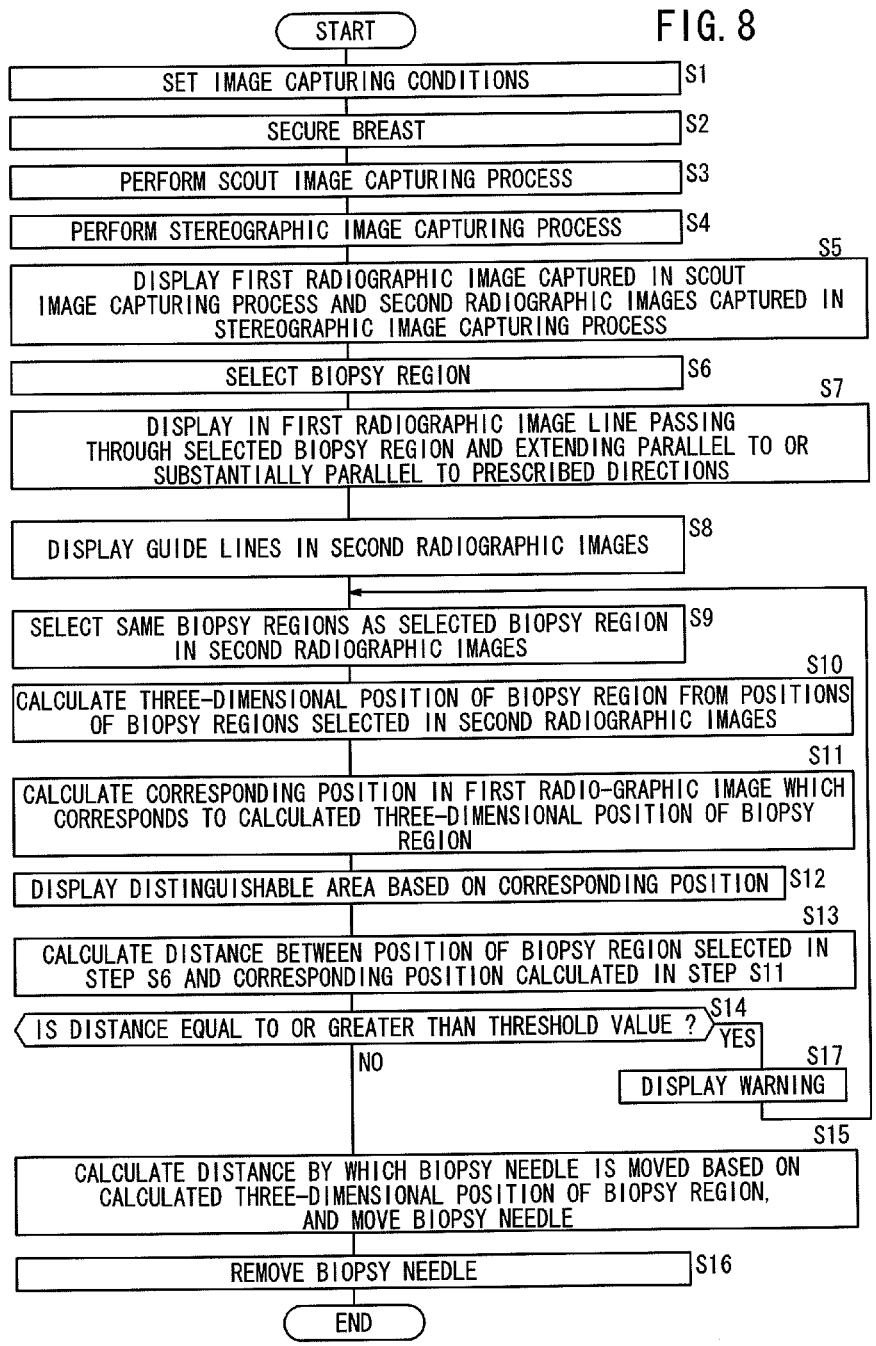
FIG. 8 is a flowchart of an operation sequence of the mammographic apparatus.

Operation of the mammographic apparatus 12 will be described below with reference to a flowchart shown in FIG. 8. Before radiographic images are captured, the image capturing condition setting unit 100 sets image capturing conditions including doses of the radiation 24 for a scout image capturing process and a stereographic image capturing process, irradiation times, image capturing angles, and imaging capturing orders for a scout image capturing process and a stereographic image capturing process, etc. in step S1.

Then, the doctor or radiological technician positions the breast 22 of the examinee 20 in step S2. Specifically, the doctor or radiological technician places the breast 22 in a predetermined position on the image capturing base 32, i.e., a position facing the opening 48, and operates the compression plate controller 108 to move the compression plate 34 toward the image capturing base 32 in the direction indicated by the arrow Z, compressing and positioning the breast 22.

The breast 22 is now compressed and secured by the image capturing base 32 and the compression plate 34. The compression plate position calculator 128 calculates the positional information of the compression plate 34 with respect to the image capturing base 32, and outputs the calculated positional information to the traveled distance calculator 130.

Then, the doctor or radiological technician turns on an exposure switch, not shown, to carry out a scout image capturing process in step S3. Specifically, the radiation source controller 104 energizes the radiation source 26 according to the image capturing conditions for the scout image capturing process from the image capturing condition setting unit 100. The radiation source 26 now emits the radiation 24. At this time, the housing unit controller 102 turns the radiation source housing unit 28 to achieve the set image capturing angle for the scout image capturing process. In the present embodiment, the housing unit controller 102 turns the radiation source housing unit 28 to bring the radiation source 26 to the position A.

The radiation 24 emitted from the radiation source 26 in the position A passes through the opening of the collimator 60 out of the radiation source housing unit 28, and is applied to the breast 22. The radiation 24 then passes through the breast 22, and is detected by the solid-state detector 30 as radiation representing a single radiographic image of the breast 22. The detector controller 110 controls the solid-state detector 30 to acquire a single radiographic image (first radiographic image) from the detected radiation. The acquired first radiographic image is sent to and acquired by the first radiographic image acquirer 112.

Then, the doctor or radiological technician turns on an exposure switch, not shown, to carry out a stereographic image capturing process in step S4. Specifically, the radiation source controller 104 energizes the radiation source 26 according to the image capturing conditions for the stereographic image capturing process from the image capturing condition setting unit 100. The radiation source 26 now emits the radiation 24. At this time, the housing unit controller 102 turns the radiation source housing unit 28 to achieve the set image capturing angles for the stereographic image capturing process. In the present embodiment, the housing unit controller 102 turns the radiation source housing unit 28 to bring the radiation source 26 successively to the position B ($+\theta1$) and the position C ($-\theta1$). When the radiation source 26 is positioned in each of the position B ($+\theta1$) and the position C ($-\theta1$), the radiation source controller 104 energizes the radiation source 26 to emit the radiation 24.

When the radiation source 26 is in the position B, the radiation 24 emitted from the radiation source 26 in the position B passes through the opening of the collimator 60 out of the radiation source housing unit 28, and is applied to the breast 22. The radiation 24 then passes through the breast 22, and is detected by the solid-state detector 30 as radiation representing a single radiographic image of the breast 22. The detector controller 110 controls the solid-state detector 30 to acquire a single radiographic image (second radiographic image) from the detected radiation. The acquired second radiographic image is sent to and acquired by the second radiographic image acquirer 114.

When the radiation source 26 is in the position C, the radiation 24 emitted from the radiation source 26 in the position C passes through the opening of the collimator 60 out of the radiation source housing unit 28, and is applied to the breast 22. The radiation 24 then passes through the breast 22, and is detected by the solid-state detector 30 as radiation representing a single radiographic image of the breast 22. The detector controller 110 controls the solid-state detector 30 to acquire a single radiographic image (second radiographic image) from the detected radiation. The acquired second radiographic image is sent to and acquired by the second radiographic image acquirer 114. In the stereographic image capturing process, therefore, the mammographic apparatus 12 acquires a plurality of (two) second radiographic images captured at different image capturing angles.

Then, the first display controller 116 displays the first radiographic image acquired by the first radiographic image acquirer 112 on the display unit 120, and the second display controller 118 displays the two second radiographic images acquired by the second radiographic image acquirer 114 on the display unit 120 in step S5. The first display controller 116 and the second display controller 118 display the first radiographic image and the second radiographic images in respective different display areas of the display unit 120.

The doctor or radiological technician operates the biopsy region selector 122 to select the biopsy region 36 in the first radiographic image while seeing the displayed first radiographic image (an image of the breast 22 as an object to be examined) in step S6. When the biopsy region 36 is selected by the biopsy region selector 122, the first display controller 116 displays a distinguishable area based on the position of the selected biopsy region 36. In the present embodiment, as shown in FIG. 7, the first display controller 116 displays the frame 200 as a distinguishable area based on the position of the selected biopsy region 36.

Then, the first display controller 116 displays, in the first radiographic image, the line 202 passing through the biopsy region 36 and extending parallel to or substantially parallel to the prescribed directions in step S7.

Then, the second display controller 118 displays, in the second radiographic images, the respective guide lines 204 passing through positions in the second radiographic images which correspond to the position of the selected biopsy region 36 in the first radiographic image and extending parallel to or substantially parallel to the prescribed directions in step S8. The guide lines 204 indicate the position in the second radiographic images of the biopsy region 36 selected in step S6 from which a sample tissue is to be removed. In other words, the guide lines 204 show that the biopsy region 36 selected in step S6 is present on the guide lines 204 or within a certain range from the guide lines 204. Each of the guide lines 204 may be a line having a certain thickness. With the guide lines 204 being thus displayed, the doctor or radiological technician finds it easy to select, in the second radiographic images, the same biopsy regions 36 as the biopsy region 36 selected in the first radiographic image, and the three-dimensional position of the biopsy region 36 selected in the first radiographic image can be calculated with high accuracy.

Then, the doctor or radiological technician operates the biopsy region selector 122 to select, in the second radiographic images, the same biopsy regions 36 as the biopsy region 36 selected in the first radiographic image in step S6 while seeing the second radiographic images with the guide lines 204 displayed thereon, in step S9.

Then, the biopsy region position calculator 124 calculates the three-dimensional position of the biopsy region 36 from the positions of the biopsy regions 36 selected in the respective second radiographic images in step S10. The corresponding position calculator 132 calculates the position (corresponding position) in the first radiographic image which corresponds to the calculated three-dimensional position of the biopsy region 36 in step S11.

Figure 9:
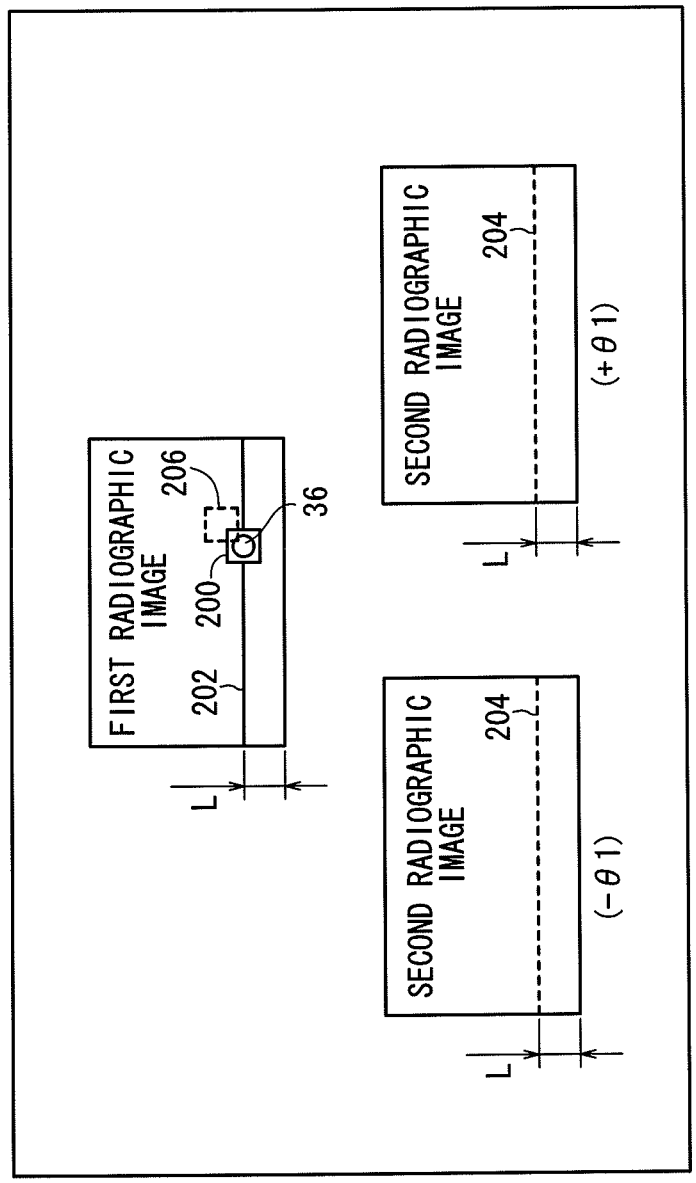
FIG. 9 is a view showing by way of example a screen displayed on a display unit in step S12 of the flowchart shown in FIG. 8.

Then, in step S12, the first display controller 116 displays a distinguishable area based on the corresponding position calculated in step S11. Specifically, the first display controller 116 displays a frame 206 as a distinguishable area based on the corresponding position. FIG. 9 shows by way of example a screen displayed on the display unit 120 in step S12. In FIG. 9, the frame 200 and the frame 206, which is of the same size as the frame 206, are displayed on the screen. The frame 200 and the frame 206 which are displayed are slightly displaced from each other. The frame 200 and the frame 206 may be of different sizes.

If the biopsy region 36 selected in the first radiographic image in step S6 and the biopsy regions 36 selected in the second radiographic images in step S9 are identical to each other, then the position of the biopsy region 36 selected in the first radiographic image in step S6 and the corresponding position calculated in step S11 are identical to each other, and hence the frame 200 and the frame 206 are fully or substantially aligned with each other. Since the distinguishable area based on the corresponding position is displayed, the doctor or radiological technician can determine to a certain extent whether the biopsy regions 36 selected in the second radiographic images are identical to the biopsy region 36 selected in the first radiographic image or not.

Then, in step S13, the distance calculator 134 calculates the distance between the position of the biopsy region 36 selected in the first radiographic image in step S6 and the corresponding position calculated in step S11.

The first display controller 116 and the traveled distance calculator 130 determine whether or not the calculated distance is equal to or greater than a predetermined threshold value in step S14. If the calculated distance is not equal to or greater than the threshold value (NO in step S14), then the traveled distance calculator 130 calculates the distance by which the biopsy needle 56 is to move with respect to the biopsy region 36, based on the three-dimensional position of the biopsy region 36, the position of the tip end of the biopsy needle 56 which has been calculated by the biopsy needle position calculator 126, and the position of the compression plate 34 which has been calculated by the compression plate position calculator 128, and the biopsy needle controller 106 moves the sampler 58 of the biopsy needle 56 to the biopsy region 36 in step S15. Thus, the biopsy needle 56 starts to sample a tissue from the biopsy region 36 under suction. Thereafter, the biopsy needle controller 106 moves the biopsy needle 56 in the direction indicated by the arrow Z to remove the biopsy needle 56 from the breast 22 in step S16. The tissue sampling process is now ended.

As described above, if the calculated distance is smaller than the threshold value, then it is judged that the biopsy region 36 selected in the first radiographic image and the biopsy regions 36 selected in the second radiographic images are identical to each other, and the tissue is sampled based on the three-dimensional position which is determined from the biopsy regions 36 selected in the second radiographic images.

If the calculated distance is equal to or greater than the threshold value, then the first display controller 116 (YES in step S14), then the first display controller 116 displays (indicates) a warning that the biopsy region 36 selected in the first radiographic image in step S6 and the biopsy regions 36 selected in the second radiographic images in step S9 are different from each other in step S17. Thereafter, control goes back to step S9. The warning may be displayed as a blinking of the frame 206 or may be displayed as a warning message or may be in the form of warning sound. Since a warning is issued when the biopsy regions 36 selected in the second radiographic images are different from the biopsy region 36 selected in the first radiographic image, the doctor or radiological technician is prompted to take notice and may select again the biopsy regions 36 in the second radiographic images. Accordingly, no tissue is unduly sampled from the breast 22.

The line 202 may not be displayed in the first radiographic image. The frame 200 may not be displayed in the first radiographic image. In this case, in step S12, the frame 200 is not displayed, but only the frame 206 is displayed. With the frame 206 being displayed, the doctor or radiological technician can visually recognize whether the position of the biopsy region 36 selected in the first radiographic image in step S6 is near the position of the frame 206 or not.

In the illustrated embodiment, if the calculated distance is judged as being equal to or greater than the distance calculated in step S14, then a warning is issued in step S17 and then control goes back to step S9. However, control may go back to step S9 without the issuance of a warning. Specifically, if the calculated distance is not judged as being equal to or greater than the distance calculated in step S14, then the first display controller 116 may indicate that the biopsy region 36 selected in the first radiographic image and the biopsy regions 36 selected in the second radiographic images are identical to each other, and then control may go to step S15.

In the illustrated embodiment, after the corresponding position is calculated in step S11, the distinguishable area based on the corresponding position is displayed in step S12. However, after the corresponding position is calculated in step S11, control may go directly to step S13, skipping step S12. If the calculated distance is judged as being equal to or greater than the threshold value in step S14, then the distinguishable area based on the corresponding position may be displayed in step S12 and then control may go to step S17.

In the illustrated embodiment, the first display controller 116 and the second display controller 118 display the first radiographic image and the second radiographic images on the same display unit 120. However, the mammographic apparatus 12 may have a first display unit for displaying the first radiographic image and a second display unit for displaying the second radiographic images, and the first display controller 116 may display the first radiographic image on the first display unit, and the second display controller 118 may display the second radiographic images on the second display unit.

Although certain preferred embodiments of the present invention have been shown and described in detail, it should be understood that various changes and modifications may be made therein without departing from the scope of the appended claims.

What is claimed is:

1. An image display apparatus comprising:
   a first radiographic image acquirer configured to acquire a first radiographic image obtained by a radiation detector that detects radiation having passed through an object to be examined, which includes a biopsy region, and that converts the detected radiation into a radiation image when the object to be examined is irradiated by a radiation source in a prescribed position, wherein said radiation source is movable in a prescribed direction with respect to the object to be examined;
   a second radiographic image acquirer configured to acquire a plurality of second radiographic images obtained by the radiation detector when the object to be examined is irradiated by the radiation source is in different positions than the prescribed position, wherein the prescribed position for acquiring the first radiographic image is used as a reference position for acquiring the plurality of second radiographic images,
   a position sensor sensing placement of the radiation source at a first acute angle from the prescribed position and at a second acute angle from the prescribed position, wherein an axis passing through the prescribed position is a line of symmetry for the first acute angle relative to the second acute angle, and the second radiographic image acquirer acquires a first one of the second radiographic images at the first acute angle and acquires a second one of the second radiographic images at the second acute angle;
   a first display controller for displaying the first radiographic image acquired by the first radiographic image acquirer on a first display unit;
   a pointing device for selecting the biopsy region of the object to be examined which is displayed on the first display unit; and
   a second display controller configured to display the second radiographic images acquired by the second radiographic image acquirer on a second display unit and, when the biopsy region is selected in the displayed first radiographic image by the pointing device, displaying, in the second radiographic images, respective guide lines passing through positions in the second radiographic images which correspond to a position of the biopsy region selected in the first radiographic image and extending parallel to the prescribed direction.

2. An image display apparatus according to claim 1, further comprising a distance calculator for calculating a distance between the corresponding position calculated by the corresponding position calculator and the position of the biopsy region selected in the first radiographic image by the user,
   wherein if the distance calculated by the distance calculator is equal to or greater than a predetermined threshold value, the first display controller indicates that the biopsy region selected in the first radiographic image and the biopsy regions selected in the second radiographic images are different from each other.

3. An image display apparatus according to claim 1, wherein in case that the biopsy region of the object to be examined is selected in the first radiographic image by the user of the image display apparatus, the first display controller displays, in the first radiographic image, a line passing through the selected biopsy region and extending parallel to the prescribed direction.

4. An image display apparatus according to claim 1, wherein the first display unit and the second display unit are provided as a single display unit, and the first display controller and the second display controller display the first radiographic image and the second radiographic images, respectively, in different display areas of the single display unit.

5. A non-transitory recording medium storing a program for enabling a computer operating with display apparatus to function as:
   a first radiographic image acquirer configured to acquire a first radiographic image obtained by a radiation detector that detects radiation having passed through an object to be examined, which includes a biopsy region, and that converts the detected radiation into a radiation image when the object to be examined is irradiated by a radiation source in a prescribed position and said radiation source is movable in a prescribed direction with respect to the object to be examined;
   a second radiographic image acquirer configured to acquire a plurality of second radiographic images obtained by the radiation detector when the object to be examined is irradiated by the radiation source which is in different positions than the prescribed position, said different positions disposed symmetrically about an axis including the prescribed position;

a first display controller for displaying the first radiographic image acquired by the first radiographic image acquirer on a first display unit;

a pointing device for selecting the biopsy region which is displayed on the first display unit; and a second display controller for displaying the second radiographic images acquired by the second radiographic image acquirer on a second display unit and, when the biopsy region is selected in the displayed first radiographic image by the pointing device, displaying, in the second radiographic images, respective guide lines passing through positions in the second radiographic images which correspond to a position of the biopsy region selected in the first radiographic image and extending parallel to the prescribed direction.

6. The image display apparatus of claim 1, wherein respective guidelines on the second radiographic images have a common displacement relative to a reference edge of respective images in each of the plurality of second radiographic images.

7. The image display apparatus of claim 6, wherein respective guidelines on the second radiographic images have a common displacement relative to the reference edge which displacement also corresponds to an equal displacement in the first radiographic image from a corresponding reference edge in the first radiographic image, said displacement from the reference edge being based on the biopsy region indicated in the first radiographic image by the pointing device.

8. The image display apparatus of claim 7,
wherein in case that the biopsy region is selected in the displayed first radiographic image by the pointing device, the first display controller displays a distinguishable area based on the position of the selected biopsy region on the first display unit; and further comprising:

a biopsy region position calculator for, in case that biopsy regions are selected in at least two of the second radiographic images by a user of the image display apparatus, calculating a three-dimensional position of the biopsy region based on the positions of the selected biopsy regions; and a corresponding position calculator for calculating a corresponding position in the first radiographic image which corresponds to the calculated three-dimensional position of the biopsy region, wherein the first display controller displays a distinguishable area based on the calculated corresponding position.

9. The image display apparatus of claim 7, wherein the pointing device is configured to accept a position of a biopsy region on at least one of the second radiographic images, and a distance calculation is determined between a corresponding position of the biopsy region indicated on the first radiographic image and position of the biopsy region indicated on the second radiographic image, and appropriateness of the biopsy region is assessed based on the calculated distance.

10. The apparatus of claim 1, further comprising a biopsy position calculator configured to calculate a three-dimensional position from the biopsy region selected by the pointing device in the first display unit and selected biopsy regions in the first one and the second one of the second radiographic images;

a corresponding region calculator configured to calculate a corresponding position in the first radiographic image which corresponds to the calculated three-dimensional position of the biopsy region, and wherein the first display controller displays a distinguishable area based on the calculated corresponding position.

* * * * *